US00PP23170P2

(12) United States Plant Patent
van der Knaap

(10) Patent No.: US PP23,170 P2
(45) Date of Patent: Nov. 6, 2012

(54) ***KALANCHOE* PLANT NAMED 'DON BASCO'**

(50) Latin Name: *Kalanchoe blossfeldiana*
Varietal Denomination: Don Basco

(75) Inventor: Leonardus Johannes Maria van der Knaap, Naaldwijk (NL)

(73) Assignee: Nubilus B.V., Naaldwijk (NL)

( * ) Notice: Subject to any disclaimer, the term of this patent is extended or adjusted under 35 U.S.C. 154(b) by 10 days.

(21) Appl. No.: 12/932,730

(22) Filed: Mar. 4, 2011

(51) Int. Cl.
*A01H 5/00* (2006.01)

(52) U.S. Cl. ..... Plt./336

(58) Field of Classification Search ..... Plt./336
See application file for complete search history.

*Primary Examiner* — Susan McCormick Ewoldt
(74) *Attorney, Agent, or Firm* — C. A. Whealy

(57) ABSTRACT

A new and distinct cultivar of *Kalanchoe* plant named 'Don Basco', characterized by its upright, uniform and vigorous growth habit; freely branching habit; dark green-colored leaves; uniform and freely flowering habit; double white-colored flowers; and good postproduction longevity.

2 Drawing Sheets

Botanical designation: *Kalanchoe blossfeldiana.*
Cultivar denomination: 'DON BASCO'.

BACKGROUND OF THE INVENTION

The present invention relates to a new and distinct cultivar of *Kalanchoe* plant, botanically known as *Kalanchoe blossfeldiana* and hereinafter referred to by the name 'Don Basco'.

The new *Kalanchoe* plant is a product of a planned breeding program conducted by the Inventor in Naaldwijk, The Netherlands. The objective of the breeding program is to create new double-flowered *Kalanchoe* plants with attractive foliage and flower coloration.

The new *Kalanchoe* plant originated from a cross-pollination made by the Inventor in Naaldwijk, The Netherlands in September, 2007, of a proprietary selection of *Kalanchoe blossfeldiana* identified as code number 20061123-001, not patented, as the female, or seed parent with a proprietary selection of *Kalanchoe blossfeldiana* identified as code number 20011350-001, not patented, as the male, or pollen, parent. The new *Kalanchoe* plant was discovered and selected by the Inventor as a flowering plant from within the progeny of the stated cross-pollination in a controlled greenhouse environment in Naaldwijk, The Netherlands in July, 2008.

Asexual reproduction of the new *Kalanchoe* plant by vegetative terminal cuttings in a controlled greenhouse environment in Naaldwijk, The Netherlands since January, 2009 has shown that the unique features of this new *Kalanchoe* plant are stable and reproduced true to type in successive generations.

SUMMARY OF THE INVENTION

Plants of the new *Kalanchoe* have not been observed under all possible environmental conditions and cultural practices. The phenotype may vary somewhat with variations in environmental conditions such as temperature, daylength and light intensity without, however, any variance in genotype.

The following traits have been repeatedly observed and are determined to be the unique characteristics of 'Don Basco'. These characteristics in combination distinguish 'Don Basco' as a new and distinct *Kalanchoe* plant:

1. Upright, uniform and vigorous growth habit.
2. Freely branching habit.
3. Dark green-colored leaves.
4. Uniform and freely flowering habit.
5. Double white-colored flowers.
6. Good postproduction longevity.

Plants of the new *Kalanchoe* can be compared to plants of the female parent selection. Plants of the new *Kalanchoe* differ primarily from plants of the female parent selection in the following characteristics:

1. Plants of the new *Kalanchoe* are larger than plants of the female parent selection.
2. Plants of the new *Kalanchoe* are more freely branching than plants of the female parent selection.
3. Plants of the new *Kalanchoe* have larger leaves than plants of the female parent selection.
4. Plants of the new *Kalanchoe* and the female parent selection differ in flower color as plants of the female parent selection have white, pink and yellow-colored flowers.

Plants of the new *Kalanchoe* can also be compared to plants of the male parent selection. Plants of the new *Kalanchoe* differ from plants of the male parent selection in the following characteristics:

1. Plants of the new *Kalanchoe* are smaller than plants of the male parent selection.
2. Plants of the new *Kalanchoe* are more freely branching than plants of the male parent selection.
3. Plants of the new *Kalanchoe* have smaller leaves than plants of the male parent selection.
4. Plants of the new *Kalanchoe* and the male parent selection differ in flower form as plants of the male parent selection have single flowers.
5. Plants of the new *Kalanchoe* and the male parent selection differ in flower color as plants of the male parent selection have reddish pink-colored flowers.

Plants of the new *Kalanchoe* can be compared to plants of the *Kalanchoe blossfeldiana* 'Don Juan', disclosed in U.S. Plant Pat. No. 17,576. In side-by-side comparisons conducted in Naaldwijk, The Netherlands, plants of the new *Kalanchoe* differed from plants of 'Don Juan' in the following characteristics:

1. Plants of the new *Kalanchoe* were more compact than plants of 'Don Juan'.
2. Plants of the new *Kalanchoe* had smaller leaves than plants of 'Don Juan'.
3. Plants of the new *Kalanchoe* and 'Don Juan' differed in flower color as plants of 'Don Juan' were red in color.

BRIEF DESCRIPTION OF THE PHOTOGRAPHS

The accompanying colored photographs illustrate the overall appearance of the new *Kalanchoe* plant showing the colors as true as it is reasonably possible to obtain in colored reproductions of this type. Colors in the photographs may differ slightly from the color values cited in the detailed botanical description which accurately describe the colors of the new *Kalanchoe* plant.

The photograph on the first sheet comprises a side perspective view of a typical flowering plant of 'Don Basco' grown in a container.

The photograph on the second sheet are close-up views of a typical flower (top), a typical inflorescence (center) and the upper and lower surfaces of typical leaves (bottom).

DETAILED BOTANICAL DESCRIPTION

The aforementioned photographs and following observations, measurements and values describe plants grown during the winter in 12-cm containers in a glass-covered greenhouse in Naaldwijk, The Netherlands and under conditions which closely approximate commercial *Kalanchoe* production. During the production of the plants, day temperatures ranged from 20° C. to 30° C., night temperatures ranged from 18° C. to 25° C. and light levels ranged from 5 kilolux to 60 kilolux. Plants received long day/short night conditions (more than 14 hours of light) for about three weeks; plants then received photoinductive short day/long night conditions (minimum 14 hours darkness) until flowering. Plants were 13 weeks old when the photographs and the description were taken. In the detailed description, color references are made to The Royal Horticultural Society Colour Chart, 2001 Edition, except where general terms of ordinary dictionary significance are used.

Botanical classification: *Kalanchoe blossfeldiana* 'Don Basco'.

Parentage:

*Female, or seed, parent*.—Proprietary selection of *Kalanchoe blossfeldiana* identified as code number 20061123-001, not patented.

*Male or pollen parent*.—Proprietary selection of *Kalanchoe blossfeldiana* identified as code number 20011350-001, not patented.

Propagation:

*Type*.—By vegetative terminal cuttings.

*Time to initiate roots, summer*.—About ten days at temperatures of 21° C.

*Time to initiate roots, winter*.—About two weeks at temperatures of 21° C.

*Time to produce a rooted young plant, summer*.—About three weeks at temperatures of 21° C.

*Time to produce a rooted young plant, winter*.—About four weeks at temperatures of 21° C.

*Root description*.—Fine, fibrous; white in color.

*Rooting habit*.—Freely branching; dense.

Plant description:

*Plant habit*.—Upright, uniform and vigorous growth habit with rounded crown; freely flowering with numerous compound cymes; appropriate for 10-cm to 13-cm containers.

*Plant height at flowering*.—About 22 cm to 24 cm.

*Plant diameter at flowering*.—About 23 cm to 27 cm.

Lateral branch description:

*Branching habit*.—Freely branching habit; usually about 15 lateral branches develop per plant.

*Length*.—About 12 cm to 15 cm.

*Diameter*.—About 1 cm.

*Internode length*.—About 1.5 cm.

*Aspect*.—Erect.

*Strength*.—Strong.

*Texture*.—Smooth, glabrous.

*Color*.—Close to 141B.

Foliage description:

*Arrangement*.—Opposite, simple; generally symmetrical.

*Length, generative plants*.—About 5 cm to 14 cm.

*Width, generative plants*.—About 3 cm to 10 cm.

*Shape*.—Ovate.

*Apex*.—Rounded acute.

*Base*.—Obtuse, rounded with truncate tendencies.

*Margin*.—Crenate.

*Texture, upper and lower surfaces*.—Glabrous, leathery; succulent.

*Venation pattern*.—Pinnate; reticulate.

*Color*.—Developing leaves, upper surface: Close to 137A. Developing leaves, lower surface: Close to 147B. Fully expanded leaves, upper surface: Close to 137A; venation, close to 137B. Fully expanded leaves, lower surface: Close to 147A; venation, close to 138A to 138B.

*Petiole*.—Length: About 1 cm to 3.5 cm. Diameter: About 5 mm. Texture, upper and lower surfaces: Smooth, glabrous. Color, upper surface: Close to 144A. Color, lower surface: Close to 147D.

Flower description:

*Flower arrangement and habit*.—Double flowers arranged singly in compound dichasial cymes arising from leaf axils; uniform and freely flowering habit with usually about 12 to 34 flowers developing per inflorescence.

*Fragrance*.—None detected.

*Natural flowering season*.—Plants of the new *Kalanchoe* initiate and develop flowers under short day/long night conditions or during the late autumn/winter/early spring; flower initiation and development can also be induced under artificial short day/long conditions (at least 14 hours of darkness).

*Time to flower*.—Under short day/long night photoinductive conditions, about 60 days are required.

*Post-production longevity*.—Excellent post-production longevity; flowers maintain good substance for about four weeks under interior environmental conditions; flowers persistent.

*Inflorescence height*.—About 4 cm.

*Inflorescence diameter*.—About 4 cm to 7.5 cm.

*Flower diameter*.—About 2 cm.

*Flower length (height)*.—About 1.2 cm.

*Flower bud*.—Shape: Ovoid. Length: About 9 mm. Diameter: About 5 mm. Color: Close to 160B.

*Petals*.—Arrangement: About 26 fused at the base; rosette. Length: About 8 mm to 12 mm. Width: About 4 mm to 5 mm. Shape: Spatulate. Apex: Apiculate. Margin: Entire. Texture, upper and lower surfaces: Smooth, glabrous; satiny. Color: When opening, upper surface: Close to 155A; center, close to 160C. When opening, lower surface: Close to 157C. Fully opened, upper surface: Close to 155D; center, occasionally close to 57D. Fully opened, lower surface: Close to 155B.

*Sepals*.—Appearance: Four fused at the base. Length: About 6 mm. Width: About 2 mm. Shape: Lanceolate. Apex: Acute. Margin: Entire. Texture, upper and lower surfaces: Smooth; glabrous. Color, upper and lower surfaces: Close to 144B.

*Peduncles*.—Length: About 3 cm to 7 cm. Diameter: About 3 mm to 4 mm. Aspect: Mostly erect. Strength: Moderately strong. Texture: Smooth, glabrous. Color: Close to 137C.

*Pedicels*.—Length: About 3 mm to 5 mm. Diameter: About 1 mm. Aspect: Erect to about 45° from vertical. Strength: Moderately strong. Texture: Smooth, glabrous. Color: Close to 146B.

*Reproductive organs*.—Androecium: Stamen number: About five per flower. Anther shape: Oval. Anther length: About 1 mm. Anther color: Close to 16A. Amount of pollen: None observed. Gynoecium: Pistil number: About four per flower. Pistil length: About 7 mm to 8 mm. Style length: About 2 mm. Style color: Close to 145C. Stigma shape: Rounded. Stigma color: Close to 151C. Ovary color: Close to 145B.

*Seed/fruit*.—Seed and fruit development have not been observed.

Temperature tolerance: Plants of the new *Kalanchoe* have been observed to tolerate temperatures from about 5° C. to about 35° C.

Pathogen/pest resistance: Plants of the new *Kalanchoe* have not been observed to be resistant to pests and pathogens common to *Kalanchoes.*

It is claimed:

1. A new and distinct *Kalanchoe* plant named 'Don Basco' as illustrated and described.

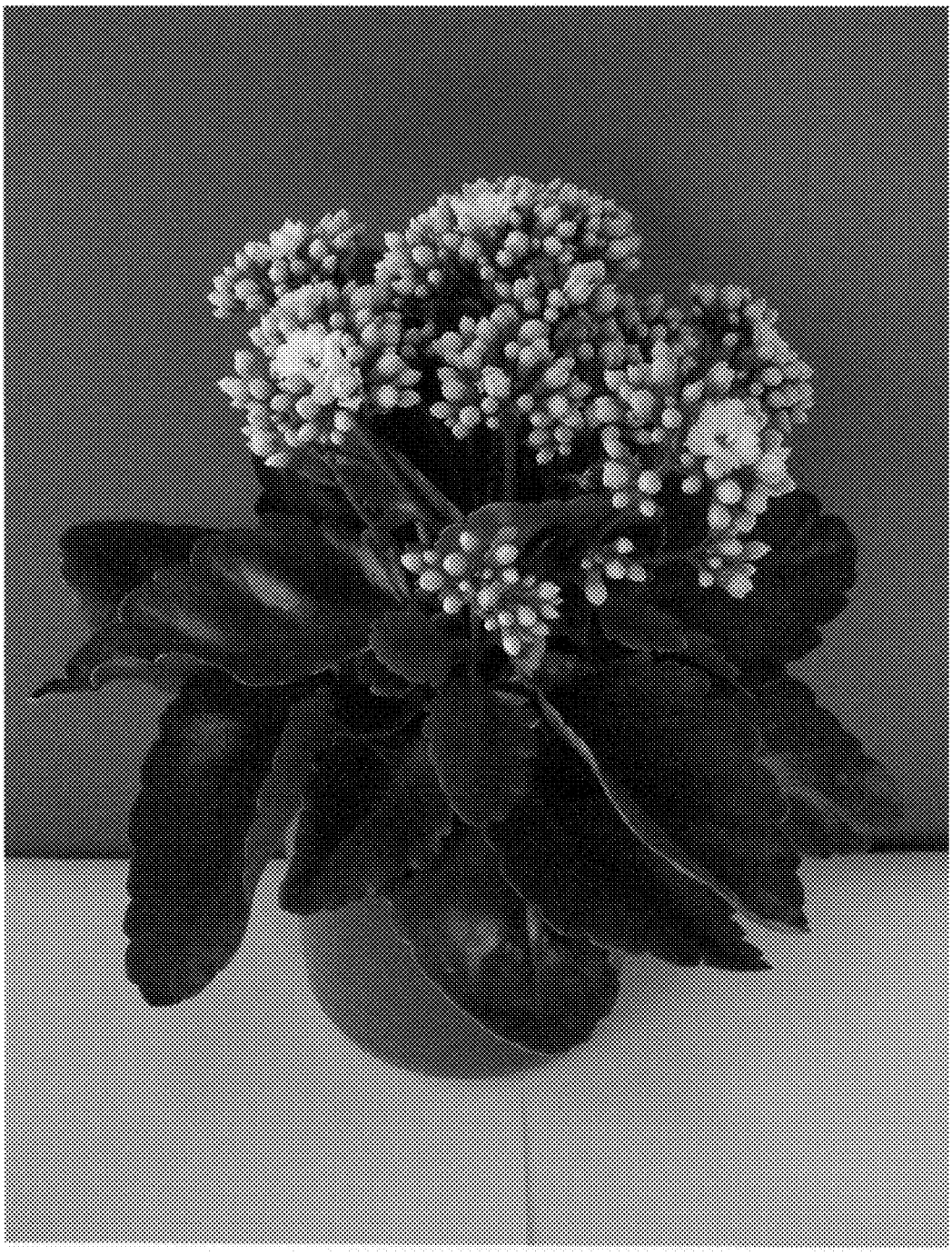

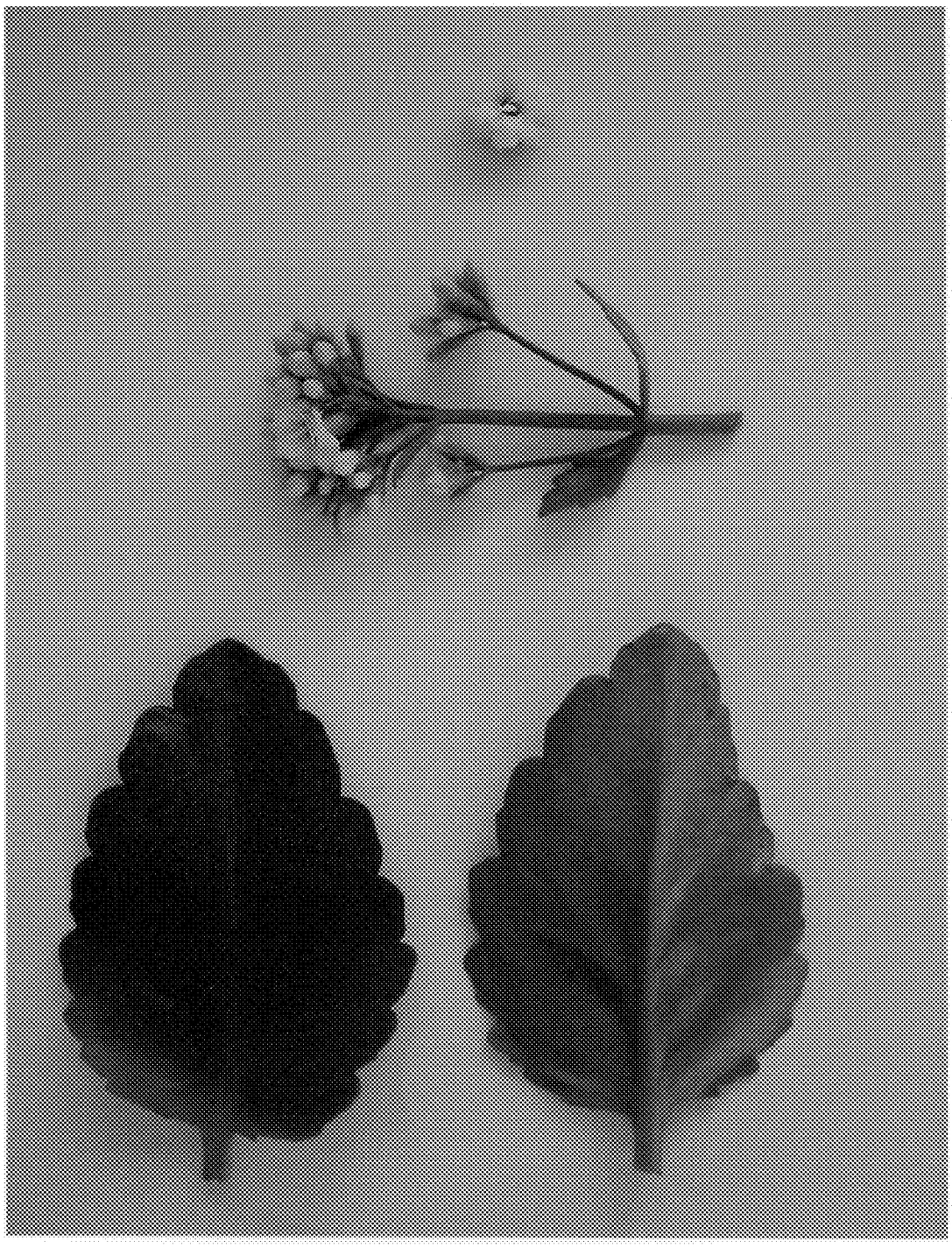

* * * * *